United States Patent [19]

Bradbury

[11] Patent Number: 5,641,793
[45] Date of Patent: Jun. 24, 1997

[54] PYRIDINE COMPOUNDS WHICH HAVE USEFUL PHARMACEUTICAL ACTIVITY

[75] Inventor: Robert Hugh Bradbury, Wilmslow, United Kingdom

[73] Assignee: Zeneca Limited, London, United Kingdom

[21] Appl. No.: 440,133

[22] Filed: May 12, 1995

[30] Foreign Application Priority Data

May 13, 1994 [GB] United Kingdom ............ 9409618

[51] Int. Cl.$^6$ ............ C07D 213/76; A61K 31/44
[52] U.S. Cl. ............ 514/352; 546/312
[58] Field of Search ............ 546/312; 514/352

[56] References Cited

U.S. PATENT DOCUMENTS

| | | | |
|---|---|---|---|
| 5,270,313 | 12/1993 | Burri et al. | 514/252 |
| 5,292,740 | 3/1994 | Burri et al. | 514/256 |
| 5,420,129 | 5/1995 | Breu et al. | 514/252 |
| 5,645,863 | 11/1995 | Chan et al. | 514/378 |

FOREIGN PATENT DOCUMENTS

| | | |
|---|---|---|
| 0510526 | 10/1992 | European Pat. Off. . |
| 0526708 | 2/1993 | European Pat. Off. . |
| 558258 | 9/1993 | European Pat. Off. . |
| 0558258 | 9/1993 | European Pat. Off. . |
| 0569193 | 11/1993 | European Pat. Off. . |
| 569193 | 11/1993 | European Pat. Off. . |
| 0601386 | 6/1994 | European Pat. Off. . |
| 0640596 | 3/1995 | European Pat. Off. . |
| 61-257960 | 11/1986 | Japan . |
| WO9009787 | 9/1990 | WIPO . |
| 9009787 | 9/1990 | WIPO . |
| 9427979 | 12/1994 | WIPO . |

OTHER PUBLICATIONS

Uhlig et al, Chemical Abstracts, vol. 100, No. 15, Abstract 131, 4205, Apr. 9, 1984, p. 672.

Himel et al, Chemical Abstracts, vol. 76, No. 1, Abstract 35787, Jan. 3, 1972, p. 318.

Himel et al., J. Agr. Food Chem., vol. 19, No. 6, 1971, pp. 1175–1180.

Igarashi et al. Abstract No. 106:133792p, Chemical Abstracts, vol. 106, Apr. 27, 1987.

Clozel et al. Pharmacological Characterization of Bosentan, a New Potent Orally Active Nonpeptide Endothelin Receptor Antagonist, J. Pharmacol. Exp. Therap. 1994, 270, 228–235.

"Endothelin Inhibitors — Advances in Therapeutic Application and Development", Philadelphia, PA, Abstracts Jun. 9–10, 1994.

Stein et al., The Discovery of Sulfonamide Endothelin Antagonists and the Development of the Orally Active ET, Antagonist 5–(Dimethylamino)–N–(3, 4–dimethyl–5–isoxazolyl)–1–naphthalenesulfonamide, Journal of Medicinal Chemistry, Feb. 4, 1994, vol. 37, No. 3, pp. 329–331.

Chan et al. Identification of a New Class of Et Selective Endothelin Antagonists by Pharmacophore Directed Screening, Biochemical and Biophysical Research Communications, May 30, 1994, vol. 201, No. 1, pp. 228–234.

R.D. Desai et al., "Studies in Sulphonamides: Part II. Preparation of $N^1$–Heterocyclic Substituted Sulphonamides from Alpha–naphthylamide and Evaluation of their Antibacterial Properties", Jour. Indian Chem. Soc. pp. 115–118, vol. 46, No. 2, 1969.

R.D. Desai et al., "Studies in Sulphonamides: Part IV. Some $N^6$–Heterocyclic Sulphonamides from 2–Naphthylamine as possible Antibacterial Agents", J. Indian Chem. Soc., pp. 411–414, vol. 46, No. 5,1969.

P. Mamalis et al., "142. Some Heterocyclic N–Oxides", J. Chem. Soc., pp. 703–705, 1950.

C. Paul Bianchi, "1–Pharmacodynamics", Chemical Abstracts, vol. 84, No. 15, 1976.

C. Paul Bianchi, "1–Pharmacology", Chemical Abstracts, vol. 106, No. 17, 1987.

Shigehara et al., "Preparation of Pyridine Derivatives and their Salts as Phospholipase $A_2$ Inhibitors", Chemical Abstracts, vol. 122, No. 25, 1995.

Primary Examiner—Zinna Northington Davis
Attorney, Agent, or Firm—Robert J. Harris

[57] ABSTRACT

The invention concerns pharmaceuticaly useful compounds of the formula I, in which Q, $A^1$, $A^2$, $A^3$, $R^1$, $R^2$, $R^3$ and $R^4$ have any of the meanings defined herein, and their pharmaceutically acceptable salts, and pharmaceutically compositions containing them. The novel compounds possess endothelin receptor antagonist activity and are useful in the treatment of diseases or medical conditions in which elevated or abnormal levels of endothelin play a significant causative role. The invention further concerns processes for the manufacture of the novel compounds and the use of the compounds in medical treatment.

10 Claims, No Drawings

PYRIDINE COMPOUNDS WHICH HAVE USEFUL PHARMACEUTICAL ACTIVITY

The present invention relates to novel pyridine derivatives and, more particularly, to novel N-(2-pyridyl)sulphonamides, and pharmaceutically-acceptable salts thereof, which possess endothelin receptor antagonist activity. These compounds are of value whenever such antagonist activity is desired, such as for research tools within pharmacological, diagnostic and related studies or in the treatment of diseases or medical conditions including, but not limited to, hypertension, pulmonary hypertension, cardiac or cerebral circulatory disease and renal disease, in warm-blooded animals (including man), in which elevated or abnormal levels of endothelin play a significant causative role. The invention also relates to pharmaceutical compositions of the novel compounds (and their salts) for use in treating said diseases or medical conditions, and to processes for the manufacture of the novel compounds. The invention further relates to the use of the novel compounds in treating one or more of the said diseases or medical conditions. A method of treating one or more of the said diseases or medical conditions using said compounds is also provided.

The endothelins are a family of endogenous 21 amino acid peptides comprising three isoforms, endothelin-1, endothelin-2 and endothelin-3. The endothelins are formed by cleavage of the $Trp^{21}$-$Val^{22}$ bond of their corresponding proendothelins by a putative endothelin converting enzyme. The endothelins are among the most potent vasoconstrictors known and have a characteristic long duration of action. They exhibit a wide range of other activities including cell proliferation and mitogenesis, extravasation and chemotaxis, and also interact with a number of other vasoactive agents. They also have direct effects on the heart. Thus the biological profile of the endothelins is consistent with a pathophysiological role in the cardiovascular system. The endothelins also have actions on other physiological systems including the airways, gastro-intestinal tract, reproductive system, kidney, liver, central nervous system, neuroendocrine system and the blood.

The endothelins are released from a range of tissue and cell sources including vascular endothelium, vascular smooth muscle, kidney, liver, uterus, airways, intestine and leukocytes. Release can be stimulated by hypoxia, shear stress, physical injury and a wide range of hormones and cytokines. Elevated endothelin levels have been found in a number of disease states in man including hypertension, pulmonary hypertension, pre-eclampsia, congestive heart failure, myocardial infarction, angina pectoris, acute and chronic renal failure, ischaemic stroke, subarachnoid haemorrhage, atherosclerosis, hypercholesterolaemia, cardiogenic and endotoxic shock, diabetes mellitus, Raynaud's disease, scleroderma, systemic sclerosis, Buerger's disease, rheumatoid arthritis, asthma, bronchitis, acute respiratory failure, liver cirrhosis, Crohn's disease, ulcerative colitis, certain cancers and after surgery.

Japanese patent application 61/257960 describes certain related sulphonamides having fungicidal activity, the compounds N-(5-chloro-2-pyridyl)-2-naphthalenesulphonamide, N-(5-chloro-2-pyridyl)-1-naphthalenesulphonamide, N-(5-trifluoromethyl-2-pyridyl)-2-naphthalenesulphonamide and N-(5-trifluoromethyl)-1-naphthalenesulphonamide being specifically described. International patent application no. 90/09787 discloses certain related sulphonamides as radiosensitizers and/or chemosensitizers. In European patent applications, publication nos. 558258 and 569193 are described certain N-(isoxazolyl)sulphonamides which are referred to as endothelin receptor antagonists.

Although a number of endothelin receptor antagonists are known, there is a continuing need for alternative antagonists. The present invention is based in part on this need and on our discovery of the unexpected antagonism of the endothelin receptor by certain N-heterocyclyl sulphonamides.

According to one aspect of the invention there is provided a compound of the formula I (set out hereinafter, together with the other chemical formulae indentified by Roman numerals) wherein Q is a naphthyl or biphenyl group;

$A^1$, $A^2$ and $A^3$ are attached to a phenyl or benzene ring of Q and are independently selected from hydrogen, (1–6C)alkyl, amino(1–6C)alkyl, hydroxy(1–6C)alkyl, N-[(1–4C)alkyl]amino(1–6C)alkyl, N,N-[di(1–4C)alkyl]amino(1–6C)alkyl, (2–6C)alkenyl, (2–6C)alkynyl, halogeno(1–6C)alkyl, (1–6C)alkoxy, dihalogeno(1–6C)alkoxy, trihalogeno(1–6C)alkoxy, (2–6C)alkenyloxy, (1–4C)alkoxy(1–6C)alkyl, (1–4C)alkylthio(1–6C)alkyl, (1–4C)alkylsulphinyl(1–6C)alkyl, (1–4C)alkylsulphonyl(1–6C)alkyl, (1–4C)alkylenedioxy, (3–6C)cycloalkyl, (3–8C)cycloalkyl(1–6C)alkyl, phenyl, phenyl(1–6C)alkyl, phenoxy, phenyl(1–6C)alkoxy, halogeno, hydroxy, mercapto, cyano, nitro, carboxy, (1–6C)alkoxycarbonyl, (2–6C)alkenyloxycarbonyl, phenyloxycarbonyl, phenyl(1–6C)alkoxycarbonyl, (1–6C)alkanoyl, benzoyl, (1–6C)alkylthio, (1–6C)alkylsulphinyl, (1–6C)alkylsulphonyl, phenylthio, phenylsulphinyl, phenylsulphonyl, (1–6C)alkanoylamino, trifluoroacetyl, trifluoroacetamido, N-[(1–4C)alkyl]trifluoroacetamido, benzamido, N-[(1–4C)alkyl]benzamido, carbamoyl, (1–4C)alkylcarbamoyl, di-(1–4C)alkylcarbamoyl, phenylcarbamoyl, sulphamoyl, N-(1–4C)alkylsulphamoyl, N,N-di(1–4C)alkylsulphamoyl, N-phenylsulphamoyl, (1–6C)alkanesulphonamido, benezenesulphonamido, ureido, 3-(1–6C)alkylureido, 3-phenylureido, thioureido, 3-(1–6C)alkylthioureido, 3-phenylthioureido and a group —NRaRb in which Ra and Rb are independently selected from hydrogen, (1–6C)alkyl, phenyl(1–4C)alkyl and (1–6C)alkyl bearing a carboxy or (1–4C)alkoxycarbonyl group, or the group —NRaRb taken together complete a 1-pyrrolidinyl, 2oxo-1-pyrrolidinyl, 1-piperidinyl or 2oxo-1-piperidinyl ring;

$R^2$, $R^3$ and $R^4$ have any of the values defined above for $A^1$, $A^2$ or $A^3$;

$R^1$ is selected from (1–6C)alkyl, amino(1–6C)alkyl, hydroxy(1–6C)alkyl, N-[(1–4C)alkyl]amino(1–6C)alkyl, N,N-[di(1–4C)alkyl]amino(1–6C)alkyl, (2–6C)alkenyl, 2-[(1–6C)alkoxycarbonyl]ethenyl, 2-phenylethenyl, (2–6C)alkynyl, (1–6C)alkoxycarbonylethynyl, phenylethynyl, halogeno(1–6C)alkyl, (1–3C)alkoxy, dihalogeno(1–3C)alkoxy, trihalogeno(1–3C)alkoxy, (2–6C)alkenyloxy, (1–4C)alkoxy(1–6C)alkyl, (1–4C)alkylthio(1–6C)alkyl, (1–4C)alkylsulphinyl(1–6C)alkyl, (1–4C)alkylsulphonyl(1–6C)alkyl, (3–6C)cycloalkyl, (3–8C)cycloalkyl(1–6C)alkyl, phenyl(1–6C)alkyl, phenyl(1–3C)alkoxy, halogeno, hydroxy, mercapto, nitro, (1–6C)alkanoyl, benzoyl, (1–6C)alkylthio, (1–6C)alkylsulphinyl, (1–6C)alkylsulphonyl, phenylthio, phenylsulphinyl, phenylsulphonyl, (1–6C)alkanoylamino, trifluoroacetyl, trifluoroacetamido, N-[(1–4C)alkyl]trifluoroacetamido, benzamido, N-[(1–4C)alkyl]benzamido, carbamoyl, (1–4C)alkylcarbamoyl, di-(1–4C)alkylcarbamoyl, phenylcarbamoyl, sulphamoyl, N-(1–4C)alkylsulphamoyl, N,N-di(1–4C)alkylsulphamoyl, N-phenylsulphamoyl, (1–6C)alkanesulphonamido, benezenesulphonamido, ureido, 3-(1–6C)alkylureido, 3-phenylureido, thioureido, 3-(1–6C)alkylthioureido, 3-phenylthioureido and a group —NRaRb in which Ra and Rb are independently selected from hydrogen, (1–6C)alkyl, phenyl(1–4C)alkyl and (1–6C)alkyl bearing a carboxy or (1–4C)alkoxycarbonyl group, or the group —NRaRb taken together complete a 1-pyrrolidinyl, 2-oxo-1-pyrrolidinyl, 1-piperidinyl or 2-oxo-1-piperidinyl ring; or $R^1$ together with the adjacent $R^2$ or $R^3$ is (3–5C)alkylene or (3–5C)alkenylene which together with the carbon atoms to which $R^1$ and $R^2$ or $R^3$ are attached complete a 5–7 membered ring;

and wherein any of said phenyl, naphthyl or benzene moieties of $A^1, A^2, A^3, R^1, R^2, R^3$ or $R^4$ may be unsubstituted or bear one or two substituents independently selected from (1–4C)alkyl, (1–4C)alkoxy, halogeno, cyano and trifluoromethyl; or a pharmaceutically-acceptable salt thereof; but excluding N-(5-chloro-2-pyridyl)-2-naphthalenesulphonamide, N-(5-chloro-2-pyridyl)-1-naphthalenesulphonamide, N-(5-trifluoromethyl-2-pyridyl)-2-naphthalenesulphonamide and N-(5-trifluoromethyl)-1-naphthalenesulphonamide.

It will be appreciated that, depending on the nature of the substituents, certain of the formula I compounds may possess one or more chiral centres and may be isolated in one or more racemic or optically active forms. It is to be understood that the present invention concerns any form of such a compound of formula I which possesses the aforementioned useful pharmacological properties, it being well known to make optically active forms, for example by synthesis from suitable chiral intermediates or by resolution, and how to determine their pharmacological properties, for example by use of the tests described hereinafter.

It will also be appreciated that a compound of formula I may exhibit polymorphism, that a compound of formula I may form a solvate and that a compound of formula I may exist in more than one tautomeric form. It is to be understood that the present invention also concerns any polymorphic form, any tautomer or any solvate, or any mixture thereof, which possesses endothelin receptor antagonist activity.

It is further to be understood that generic terms such as "alkyl" include both straight and branched chain variants when the carbon numbers permit.

However, when a particular radical such as "propyl" is given, it is specific to the straight chain variant, branched chain variants such as "isopropyl" being specifically named when intended. The same convention applies to other radicals.

Particular values for $A^1, A^2, A^3, R^1, R^2, R^3$ or $R^4$ where appropriate include, by way of example, for (1–6C)alkyl: (1–4C)alkyl, such as methyl, ethyl, propyl, isopropyl and sec-butyl;

for amino(1–6C)alkyl: amino(1–4C)alkyl, such as aminomethyl and 2-aminoethyl;

for hydroxy(1–6C)alkyl: hydroxy(1–4C)alkyl, such as hydroxymethyl, 1-hydroxyethyl and 2-hydroxyethyl;

for N-[(1–4C)alkyl]amino(1–6C)alkyl: N-[(1–2C)alkylamino(1–4C)alkyl, such as methylaminomethyl and methylaminoethyl;

for N,N-[di(1–4C)alkyl]amino(1–6C)alkyl: N,N-[di(1–2C)alkyl]amino(1–4C)alkyl, such as dimethylaminomethyl and 2-(dimethylamino)ethyl;

for (2–6C)alkenyl: (2–4C)alkenyl, such as vinyl, allyl, 1-propenyl and 2-butenyl;

for 2-[(1–6C)alkoxycarbonyl]ethenyl: 2-[(1–4C)alkoxycarbonyl]ethenyl, such as 2-methoxycarbonylethenyl and 2-ethoxycarbonylethenyl;

for (2–6C)alkynyl: (2–4C)alkynyl, such as ethynyl, 1-propynyl, 2-propynyl and 1-butynyl;

for (1–6C)alkoxycarbonylethynyl: (1–4C)alkoxycarbonylethynyl, such as methoxycarbonylethynyl and ethoxycarbonylethynyl;

for halogeno(1–6C)alkyl: halogeno(1–4C)alkyl, such as chloromethyl, bromomethyl, fluoromethyl, dichloromethyl, difluoromethyl, trifluoromethyl, 2,2,2-trifluoroethyl and pentafluoroethyl;

for (1–6C)alkoxy: (1–4C)alkoxy, such as methoxy, ethoxy, propoxy, isopropoxy and butoxy;

for (1–3C)alkoxy: methoxy and ethoxy;

for di- or tri-halogeno(1–6C)alkoxy: di- or trihalogeno(1–4C)alkoxy, such as difluoromethoxy, trifluoroethoxy, 2,2,2-trifluoroethoxy, 3,3,3-trifluoropropoxy and pentafluoroethoxy;

for di- or trihalogeno(1–3C)alkoxy: difluoromethoxy, trifluoroethoxy, 2,2,2-trifluoroethoxy and pentafluoromethoxy;

for (2–6C)alkenyloxy: (2–4C)alkenyloxy, such as vinyloxy, allyloxy, 1-propenyloxy and 2-butenyloxy;

for (1–4C)alkoxy(1–6C)alkyl: (1–2C)alkoxy(1–4C)alkyl, such as methoxymethyl, ethoxymethyl, 1-methoxyethyl, 2-methoxyethyl, 2-ethoxyethyl and 3-methoxypropyl;

for (1–4C)alkylthio(1–4C)alkyl: methylthiomethyl, 1-methylthioethyl, 2-methylthioethyl, 2-methylthioprop-2-yl, ethylthiomethyl,1-ethylthioethyl, 2-ethylthioethyl and 2-ethylthioprop-2-yl;

for (1–4C)alkylsulphinyl(1–4C)alkyl: methylsulphinylmethyl, 1-methylsulphinylethyl, 2-methylsulphinylethyl, 2-methylsulphinylprop-2-yl, ethylsulphinylmethyl, 1-ethylsulphinylethyl, 2-ethylsulphinylethyl and 2-ethylsulphinylprop-2-yl;

for (1–4C)alkylsulphonyl(1–4C)alkyl: methylsulphonylmethyl, 1-methylsulphonylethyl, 2-methylsulphonylethyl, 2-methylsulphonylprop-2-yl, ethylsulphonylmethyl, 1-ethylsulphonylethyl, 2-ethylsulphonylethyl and 2-ethylsulphonylprop-2-yl;

for (1–4C)alkylenedioxy: methylenedioxy, ethylenedioxy and isopropylidenedioxy;

for (3–6C)cycloalkyl: cyclopropyl, cyclobutyl and cyclopentyl;

for (3–8C)cycloalkyl(1–6C)alkyl: (3–5C)cycloalkyl(1–2C)alkyl, such as cyclopropylmethyl, cyclopropylethyl, cyclobutylmethyl and cyclopentylmethyl;

for phenyl(1–6C)alkyl: phenyl(1–4C)alkyl, such as benzyl, 1-phenylethyl and 2-phenylethyl;

for phenyl(1–6C)alkoxy: phenyl(1–4C)alkoxy, such as benzyloxy, 1-phenylethoxy, 2-phenylethoxy, 2-phenylpropoxy and 3-phenylpropoxy;

for phenyl(1–3)alkoxy: benzyloxy, 1-phenylethoxy and 2-phenylethoxy;

for halogeno: fluoro, chloro, bromo and iodo;

for (1–6C)alkoxycarbonyl: (1–4C)alkoxycarbonyl, such as methoxycarbonyl, ethoxycarbonyl and propoxycarbonyl;

for (3–6C)alkenyloxycarbonyl: allyloxycarbonyl, 2-methyl-2-propenyloxycarbonyl and 3-methyl-3-butenyloxycarbonyl;

for phenyl(1–4C)alkoxycarbonyl: benzyloxycarbonyl, 1-phenylethoxycarbonyl and 2-phenylethoxycarbonyl;

for (1–6C)alkanoyl: (1–4C)alkanoyl, such as formyl, acetyl and propionyl;

for (1–6C)alkylthio: (1–4C)alkylthio, such as methylthio and ethylthio;

for (1–6C)alkylsulphinyl: (1–4C)alkylsulphinyl, such as methylsulphinyl and ethylsulphinyl;

for (1–6C)alkylsulphonyl: (1–4C)alkylsulphonyl, such as methylsulphonyl and ethylsulphonyl;

for (1–6C)alkanoylamino: (1–4C)alkanoylamino, such as formamido, acetamido and propionamido;

for N-[(1–4C)alkyl]trifluoroacetamide: N-methyltrifluoroacetamide and N-ethyltrifluoroacetamide;

for N-[(1–4C)alkyl]benzamido: N-methylbenzamido and N-ethylbenzamido;

for (1–4C)alkylcarbamoyl: N-methylcarbamoyl and N-ethylcarbamoyl;

for di(1–4C)alkylcarbamoyl: N,N-dimethylcarbamoyl and N,N-diethylcarbamoyl;

for N-(1–4C)alkylthio(1–4C)alkyl:alkylsulphamoyl: N-methylsulphamoyl and N-ethylsulphamoyl for N,N-di(1–4C)alkylsulphamoyl: N,N-dimethylsulphamoyl and N,N-diethylsulphamoyl;

for (1–6C)alkanesulphonamido: (1–4C)alkanesulphonamido, such as methanesulphonamido and ethanesulphonamido;

for 3-(1–6C)alkylureido: 3-(1–4C)alkylureido, such as 3-methylureido, 3-ethylureido and 3-propylureido;

for 3-(1–6C)alkylthioureido: 3-(1–4C)alkylthioureido, such as 3-methylthioureido, 3-ethylthioureido and 3-propylthioureido;

A particular value for $R^1$ together with $R^2$ or $R^3$ when it is (3–5C)alkylene or (3–5C)alkenylene includes, for example, trimethylene, tetramethylene, 1-propenylene and 2-propenylene.

A particular value for Ra or Rb includes, by way of example, for (1–6C)alkyl: (1–4C)alkyl, such as methyl, ethyl and propyl;

for (1–6C)alkyl bearing a carboxy or (1–4C)alkoxycarbonyl group: (1–4C)alkyl bearing a carboxy or (1–2C)alkoxycarbonyl group, such as carboxymethyl, carboxyethyl, methoxycarbonylmethyl, methoxycarbonylethyl, ethoxycarbonylethyl, ethoxycarbonylethyl, methoxycarbonylpropyl and ethoxycarbonylpropyl;

for phenyl(1–4C)alkyl: benzyl, 1-phenylethyl and 2-phenylethyl.

A particular value for a substituent on a phenyl, naphthyl or benzene moiety of $A^1$, $A^2$, $A^3$, $R^1$, $R^2$, $R^3$ or $R^4$ includes by way of example, for (1–4C)alkyl: methyl and ethyl;

for (1–4C)alkoxy: methoxy and ethoxy; and for halogeno: fluoro, chloro, bromo and iodo.

Particular values for Q are, for example, naphthyl (especially naphth-1-yl and naphth-2-yl) or ortho-biphenyl.

A group of values for $R^1$ of interest include, for example, (1–4C)alkyl, amino(1–4C)alkyl, hydroxy(1–4C)alkyl, N-(1–4C)alkylamino(1–4C)alkyl, N,N-di(1–4C)alkylamino(1–4C)alkyl, halogeno, halogeno(1–4C)alkyl, (2–6C)alkenyl, (2–6C)alkynyl, nitro, phenyl(1–4C)alkyl, (3–6C)cycloalkyl, (3–8C)cycloalkyl(1–4C)alkyl, (1–6C)alkanoylamino and a group —NRaRb in which Ra and Rb are independently selected from hydrogen, (1–4C)alkyl and phenyl(–4C)alkyl.

A sub-group of values for $R^1$ of particular interest include, for example, halogeno, (1–4C)alkyl, nitro, halogeno(1–4C)alkyl, amino(1–4C)alkyl, hydroxy(1–4C)alkyl, N-(1–4C)alkylamino(1–4C)alkyl and N,N-di(1–4C)alkylamino(1–4C)alkyl.

Values for $R^1$ which are preferred include, for example, halogeno, (1–4C)alkyl, trifluoromethyl and nitro, especially halogeno.

A group of values for $R^2$, $R^3$ or $R^4$ of interest include, for example, hydrogen, (1–4C)alkyl, amino(1–4C)alkyl, hydroxy(1–4C)alkyl, N-(1–4C)alkylamino(1–4C)alkyl, N,N-di(1–4C)alkylamino(1–4C)alkyl, (1–4C)alkoxy, halogeno, halogeno(1–4C)alkyl, nitro, phenyl(1–4C)alkyl, (1–6C)alkanoylamino and a group —NRaRb in which Ra and Rb are independently selected from hydrogen, (1–6C)alkyl and phenyl(1–4C)alkyl.

A sub-group of values for $R^2$, $R^3$ or $R^4$ of particular interest include, for example, hydrogen, halogeno, (1–4C)alkoxy and (1–4C)alkyl, especially hydrogen, methyl, chloro and bromo.

A group of values for $A^1$, $A^2$ or $A^3$ of interest include for example, hydrogen, (1–4C)alkyl, halogeno, halogeno(1–4C)alkyl, nitro, (1–4C)alkanoylamino, (1–4C)alkoxy, phenyl(1–4C)alkoxy, hydroxy, carboxy, (1–4C)alkoxycarbonyl, (1–4C)alkyl bearing an amino, hydroxy, N-(1–4C)alkylamino or N,N-di(1–4C)alkylamino group, and a group —NRaRb in which Ra and Rb are independently selected from hydrogen, (1–6C)alkyl and phenyl(1–4C)alkyl.

A combination of values for $A^1$, $A^2$ and $A^3$ which is of particular interest includes, for example, when one or two of $A^1$, $A^2$ and $A^3$ are hydrogen, and the remainder of $A^1$, $A^2$ and $A^3$ have any of the values defined above.

A particular value for $(A^1)(A^2)(A^3)Q$ includes for example, $(A^1)(A^2)(A^3)Q$ in which at least one of $A^1$, $A^2$ and $A^3$ is other than hydrogen and Q has any of the values defined above.

A preferred value for $(A^1)(A^2)(A^3)Q$ includes, for example, 5-N,N-di(1–4C)alkylaminonaphth-1-yl, such as 5-dimethylaminonaphth-1-yl.

A particular group of compounds of the formula I includes, for example, compounds in which Q is naphthyl attached to the sulphonamide linkage at the 1- or 2-position of the naphthyl ring and $A^1$, $A^2$, $A^3$, $R^1$, $R^2$, $R^3$ and $R^4$ have any of the values defined above.

A further particular group of compounds of the invention includes, for example, compounds of formula Ia, or a pharmaceutically acceptable salt thereof, in which $A^4$ and $A^5$ are independently selected from any of the meanings defined hereinbefore for $A^1$, $A^2$ or $A^3$; n and m are independently selected from zero, 1, 2 or 3, provided the sum of n+m is zero, 1, 2 or 3; Ry has any of the meanings defined hereinbefore for $R^1$; $R^5$, $R^6$, $R^7$ have any of the meanings defined hereinbefore for $R^2$, $R^3$ and $R^4$ respectively. A sub-group of compounds of formula Ia includes, for example, compounds in which m=zero and n=1 or 2. A further sub-group of compounds of the formula Ia includes, for example, compounds in which m=zero, n=1 and $A^4$ is attached at the 5-position of the naphthyl ring. A further sub-group of compounds of formula Ia includes, for example, those compounds in which the naphthyl group is attached to the sulphonamido moiety at the 1-position of the naphthyl ring. Within these groups, compounds in which $A^4$ is, for example, the group —NRaRb in which Ra and Rb have any of the meanings defined hereinbefore (such as dialkylamino, for example dimethylamino) are preferred. It will be appreciated that when there is more than one $A^4$ present, the values for each $A^4$ may be the same or different. The same applies to $A^5$ when there is more than one $A^5$ present.

Groups of compounds of the invention of particular interest include, for example, compounds of the formula Ia wherein m=0; n=1;

$A^4$ is attached at the 5-position of the naphthyl ring, which ring is attached to the sulphonamido moiety at the 1-position, and $A^4$ is selected from (i) (1–4C)alkanoylamino (such as acetylamino);
(ii) the group —NRaRb in which Ra and Rb are the same and are selected from methyl, ethyl and propyl (especially methyl);
(iii) the group —NRaRb in which one of Ra and Rb is methyl and the other is ethyl or propyl; and
(iv) the group —NRaRb in which one of Ra and Rb is hydrogen and the other is methyl, ethyl, propyl, isopropyl, isobutyl and sec-butyl (especially ethyl and isopropyl); and $R^5$, $R^6$ and $R^7$ have any of the meanings defined hereinbefore for $R^2$, $R^3$ and $R^4$ respectively.

A further particular group of compounds of the invention includes, for example, compounds of formula Ib, or a pharmaceutically acceptable salt thereof, in which $A^6$ and $A^7$ are independently selected from any of the values defined hereinbefore for a value of $A^1$, $A^2$ or $A^3$; p and q are independently selected from zero, 1, 2 or 3, provided the sum of p+q is zero, 1, 2 or 3; Rz has any of the meanings defined hereinbefore for $R^1$; and $R^8$, $R^9$ and $R^{10}$ have any of the meanings defined hereinbefore for $R^2$, $R^3$ and $R^4$ respectively. A particular sub-group of compounds of formula Ib includes, for example, those compounds in which p=zero and q=1 or 2, especially those compounds in which p=0; q=1 and $A^7$ is attached at the para position of the phenyl ring and is selected from hydrogen and (1–4C)alkyl, such as methyl, ethyl, propyl, isopropyl, isobutyl or sec-butyl (especially isobutyl). It will be appreciated that when there is more than one $A^6$ present, the values for each $A^6$ may be the same or different. The same applies to $A^7$ when there is more than one $A^7$ present.

Further groups of compounds of the invention may be obtained by combining any of the abovementioned particular or generic values for Q, $A^1$, $A^2$, $A^3$, $R^1$, $R^2$, $R^3$ and $R^4$.

Compounds of the invention which are of particular interest include, for example, the specific embodiments set out hereinafter in the accompanying Examples. Of these, the compounds of formula I disclosed in Examples 1, 3, 6 and 7 are of special interest and these compounds, or a pharmaceutically-acceptable salt thereof, are provided as a further feature of the invention.

Suitable pharmaceutically-acceptable salts include, for example, salts with alkali metal (such as sodium, potassium or lithium), alkaline earth metals (such as calcium or magnesium), ammonium salts, and salts with organic bases affording physiologically acceptable cations, such as salts with methylamine, dimethylamine, trimethylamine, piperidine and morpholine. In addition, for those compounds which are sufficiently basic suitable pharmaceutically-acceptable salts include, pharmaceutically-acceptable acid-addition salts with hydrogen halides, sulphuric acid, phosphoric acid and with organic acids such as citric acid, maleic acid, methanesulphonic acid and p-toluenesulphonic acid. Alternatively, the compound of formula I may exist in a zwitterionic form.

The compounds of formula I may be obtained by standard procedures of organic chemistry well known in the art for the production of structurally analogous compounds. Such procedures are provided as a further feature of the invention and include, by way of example, the following procedures in which the generic radicals have any of the values given above, unless stated otherwise.

(a) an amine (or an alkali metal salt thereof) of the formula II is reacted with a sulphonyl halide of formula III in which Hal. is a halogeno group (for example, chloro, bromo or iodo) in a suitable solvent.

A suitable solvent includes, for example, pyridine. A catalyst, such as 4-dimethylaminopyridine or 4-pyrrolidinopyridine, may be added to assist the coupling reaction. The reaction is generally carried out at a temperature in the range of, for example, 0° C. to 120° C. and more generally 20° C. to 120° C. Alternatively a solvent such as dichloromethane, chloroform, dimethoxyethane, tetrahydrofuran or dioxan may be used in the presence of a suitable inorganic base, such as sodium or potassium carbonate (which may be present as an aqueous solution) or an organic base, for example a tertiary amine such as pyridine or triethylamine. When the alkali metal salt of the amine of formula II is used, this may be formed, for example, with the use of a suitable base such as lithium diisopropylamide at a temperature, for example, about −60° C., or sodium hydride, for example, at ambient temperature, prior to the addition of the sulphonyl halide. However it will be appreciated that the reaction of a sulphonyl halide with an amine to form a sulphonamide (and the type of solvents and conditions used therein) is well-known in the art.

Alternatively an amine (or alkali metal salt thereof) of the formula II may be reacted with a sulphonate of the formula IIIa in which Re is an electron deficient phenyl group, for example a phenyl group bearing one or more electron withdrawing groups, such as nitro or cyano, in a suitable solvent. A preferred value for Re includes, for example, 4-nitrophenyl. The reaction is carried out under similar conditions to those described above.

(b) a compound of the formula IV in which L is a suitable leaving group (such as chloro, bromo, iodo, methanesulphonyloxy or p-toluenesulphonyloxy) is reacted with a sulphonamide of the formula V. The reaction is generally carried out in the presence of a base, such as an alkali metal alkoxide (such as sodium methoxide, potassium methoxide, sodium ethoxide or potassium ethoxide) or an alkali metal hydride (such as sodium or potassium hydride), or an organic base such as diisopropylethylamine. The reaction may also be carried out using a pre-formed alkali metal salt of a compound of the formula V. A suitable inert organic solvent is usually employed, for example, N,N-dimethylformamide or N-methylpyrrolidone. The reaction is generally carried out at a temperature in the range of, for example, 20° C. to 120° C.

Sulphonyl halides of formula III are well known in the art or may be obtained, for example, by the procedures described in European patent application, publication no. 558258 and 569193, or by analogy therewith. They may also be obtained by reaction of a compound $(A^1)(A^2)(A^3)Q.NH_2$ with sodium nitrite and hydrochloric acid to form a diazonium salt, followed by reaction of the diazonium salt with sulphur dioxide in dioxan and work-up with a haloacid. Compounds of the formula IIIa may be obtained from the corresponding sulphonyl chloride by reaction with the appropriate phenol (Re.OH) using conventional procedures, for example, by heating in pyridine. Compounds of formula II and IV are commercially available or are also well-known in the art, being described in standard works of heterocyclic chemistry such as those edited by Elderfield or Wiessberger, and others can be obtained by analogy therewith using standard procedures of organic chemistry. The sulphonamides of formula V may be obtained from corresponding compounds of formula III using standard procedures.

(c) for a compound of the formula I in which Q is biphenyl, a compound of the formula VI in which T is a bromo, iodo or trifluoromethanesulphonyloxy group and the phenyl ring bearing T is optionally substituted is reacted with an optionally substituted phenylboronic acid (or an anhydride or ester thereof) in the presence of a suitable base and in the presence of a palladium(O), palladium(II), nickel(O) or nickel(II) catalyst. It will be appreciated that the optional substituents on the ring bearing T and those on the phenyl boronic acid are selected from any of the values for $A^1$, $A^2$ and $A^3$ defined hereinbefore, but that the sum of the number of substituents on the two rings can be no greater than three.

A preferred value for T is bromo or iodo.

Suitable catalysts include, for example, tetrakis(triphenylphosphine)-nickel(O), bis(triphenylphosphine)nickel(II)chloride, nickel(II)chloride, bis(triphenylphosphine)palladium(II)chloride, tetrakis(triphenylphosphine)palladium(O) and palladium(II) chloride, particularly the latter two catalysts and especially palladium(II)chloride.

A suitable base for use in the reaction is, for example, an alkali metal alkoxide such as sodium methoxide or sodium ethoxide, an alkali metal hydroxide such as sodium or potassium hydroxide, an alkali metal carbonate such as sodium or potassium carbonate, or an organic base such as a tri(1–6C)alkylamine, for example, triethylamine. A preferred base is an alkali metal carbonate, triethylamine or a mixture thereof.

The reaction may also be carried out in the presence of a suitable radical initiator, for example, azo(bisisobutyronitrile).

The process is generally performed in the presence of a suitable solvent or diluent, for example, a hydrocarbon, such as toluene or xylene, an ether, such as dioxan or tetrahydrofuran, an (1–4C)alcohol such as methanol, ethanol or butanol, water, or mixtures thereof.

The reaction is generally performed at a temperature in the range, for example, 50°–150° C., and conveniently at or about the reflux temperature of the solvent or mixture of solvents used.

Whereafter, a compound of the formula I may be converted into another compound of the formula I by conventional functional group interconversion. It will be appreciated that it may be necessary to protect one or more functional groups with a suitable protecting group prior to carrying out the process of (a), (b) or (c) above, or prior to carrying out a functional group interconversion, followed by removal of the protecting group. Suitable protecting groups and procedures for their use, together with procedure for removing the protecting group, are well known in the art, for example as described in "Protective Groups in Organic Syntheses" by Theodora Green (John Wiley and Sons Inc., 1981).

Whereafter, when a pharmaceutically-acceptable salt of a compound of formula I is required, it may be obtained, for example, by reaction with the appropriate base affording a physiologically-acceptable cation, or with the appropriate acid affording a physiologically-acceptable amine, or by any other conventional salt formation procedure.

Further, when an optically active form of a compound of formula I is required, one of the aforesaid processes may be carried out using an optically active starting material. Alternatively, the racemic form of a compound of formula I may be resolved, for example by reaction with a optically active form of a suitable organic base, for example, ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid using a conventional procedure, for example using an aqueous mineral acid such as dilute hydrochloric acid.

As stated above, the compounds of formula I will have beneficial pharmacological effects in warm-blooded animals (including man) in diseases and medical conditions where elevated or abnormal levels of endothelin play a significant causative role. (References to studies supporting the implication of endothelin in various diseases or medical conditions are, for example, disclosed in International Patent Applications, Publication Nos. WO 93/21219 and WO 94/02474.) The compounds of the invention will thus be useful in the treatment of diseases or medical conditions such as hypertension, pulmonary hypertension, congestive heart failure, dyslipidaemia, atherosclerosis, restenosis, acute and chronic renal failure, ischaemic stroke, subarachnoid haemorrhage, intermittent claudication, critical limb ischaemia, asthma, and organ failure after general surgery or translantation. They may also be useful for the treatment of pre-eclampsia, premature labour, myocardial infarction, angina pectoris, dysrrhythmia, cardiogenic and endotoxin shock, diabetes mellitus, Raynaud's disease, scleroderma, Buerger's disease, systemic sclerosis, bronchitis, acute respiratory distress syndrome, liver cirrhosis, osteoporosis, Crohn's disease, ulcerative colitis, irritable bowel syndrome, urinary incontinence, migraine, glaucoma and arthritis.

A further feature of the present invention is the use of a compound of the formula I, or a pharmaceutically acceptable salt thereof, in the manufacture of a medicament for use in the treatment of one or more of the aforesaid diseases or medical conditions.

The invention also includes the use of
N-(5-chloro-2-pyridyl)-2-naphthalenesulphonamide,
N-(5-chloro-2-pyridyl)-1-naphthalenesulphonamide,
N-(5-trifluoromethyl-2-pyridyl)-2-naphthalenesulphonamide or
N-(5-trifluoromethyl-2-pyridyl)-1-naphthalenesulponamide,
in the manufacture of a medicament for use in the treatment of one or more of the aforesaid diseases or medical conditions.

The endothelin receptor antagonist activity of the compounds of the invention may be assessed using one or more of the following procedures:

Test A:

The endothelin receptor antagonist activity of compounds of formula I may be assessed in vitro by their ability to inhibit binding of [$^{125}$I]-Endothelin-1 to its receptors. Human $ET_A$ or $ET_B$ receptors (sub-types of the endothelin receptor) were expressed in Mouse Erythroleukemic Cells (MEL cells) by using standard molecular techniques (for example, as described by Sambrook J., Fritsch E. F. & Maniatis T. (1989) Molecular Cloning: A Laboratory Manual, 2nd Edition, Cold Spring Harbor Press, U.S.A.). cDNA sequences encoding the human $ET_A$ and $ET_B$ receptor (Hosoda K. et al (1991), FEBS Lett., 287, 23–26 and Sakamoto A. et al, (1991), Biochem. Biophys Res. Comm., 178, 656–663) are subcloned into pBluescript vector followed by insertion into the MEL cell expression vector pEV as described by Needham et al (1992), Nuc. Acids Res., 20, 997–1003. The resultant expression vector was transfected into MEL cells by electroporation using procedures described by Shelton et al., (1993), Receptors and Channels, 1, 25–37. MEL cells expressing the recombinant human $ET_A$ or $ET_B$ receptor were grown in Dulbecco's Modified Eagle's Medium (DMEM) with 10% Fetal Calf Serum (FCS), 1% glutamine, 1% penicillin/streptomycin and 2 mg/ml Gibco Geneticin (G-418) sulphate. After 3–6 days induction with 1% $\underline{N},\underline{N}$-dimethylsuphoxide, the MEL cells were harvested for membrane preparation. Freshly prepared MEL cell pellets ($3\times10^9$ cells) were homogenised in 30 ml of buffer containing 50 mM 2-amino-2-(hydroxymethyl)-1,3-propanediol hydrochloride (Tris HCl), 0.19M sucrose, 5 µg/ml soybean trypsin inhibitor, 100 µg/ml bacitracin, 1 mM benzamidine and 1 mM phenanthroline pH 7.4 at 5° C. Unbroken cells and nuclei were sedimented by centrifuging the homogenate at 1500×g for 15 minutes at 5° C. The membrane pellet was resuspended in buffer and stored in liquid nitrogen until use.

[$^{125}$I]-Endothelin-1 binding to MEL cell membranes was measured in incubation buffer containing 50 mM Tris HCl, 1 mM $CaCl_2$, 0.05% polyoxyethylenesorbitan monolaurate, 0.1% Bovine Serum Albumin (BSA), 0.02% sodium azide pH 7.4 at 30° C. after 180 minutes incubation. Membrane suspension (equivalent to 1.5 µg and 0.5 µg protein/tube $ET_A$ and $ET_B$ receptor respectively) was added to the incubation containing test compound and 30pM[$^{125}$I]-Endothelin-1 in a total volume of 225 µl. Nonspecific binding was measured in the presence of 100 nM unlabelled Endothelin-1. The incubation was terminated by harvesting the incubation with 50 mM Tris pH 7.4 through a GF/B filter on a Brandel cell harvestor. The filter discs were punched out and counted in a gamma counter. Compounds are tested in triplicate over a range of concentrations and $IC_{50}$ (or $pIC_{50}$) values calculated.

In general, compounds of formula I as defined above show inhibition in Test A at a concentration of about 10 micromolar or much less.

Test B:

The endothelin receptor antagonist activity of compounds of formula I may be assessed in vitro in isolated tissues by their ability to inhibit the relaxant response to endothelin-1 in the guinea-pig isolated taenia coli. Guinea pigs of either sex and weight >250 g are killed by cervical dislocation and the caecum removed and placed in cold oxygenated Krebs solution. Strips of taenia coli are dissected out and approximately 4 cm lengths set up for isotonic recording in a 20 ml organ bath containing oxygenated Krebs solution at 32° C. After a 0–120 minute equilibration period to allow the tissue to spontaneously develop an increased tone, a cumulative concentration-response curve (relaxation) is constructed to endothelin-1 (0.3–10 nM). The tissue is then washed for a period of at least 90 minutes before construction of a second concentration-response curve to endothelin-1 in the presence of the test compound. The test compound is added to the organ bath (at an initial concentration of 20 µM) at least 30 minutes before constructing the second concentration-response curve to endothelin-1. The endothelin-1 concentration ratio for each experiment is determined by comparing the most parallel portions of the control and drug treated concentration-response curves. From this a $pA_2$ is calculated: $pA_2=-\log[\text{molar drug concentration}]+\log[\text{concentration ratio}-1]$.

Test C:

This in vivo test involves the measurement of the antagonist effect of the test compound against the pressor response induced by intravenously-administered proendothelin-1 in a pithed rat preparation.

Male rats (280–330 g) are anaesthetised with halothane and artificially respired through a tracheal cannula. Rats are pithed by passing a 2 mm diameter needle through the orbit, through the foramen magnum, and down into the spinal canal. The left femoral vein and the right carotid artery are isolated and catheters filled with heparinised saline are implanted for administration of compounds and measurement of blood pressure respectively. Body temperature is maintained at 38° C. (as measured rectally) by a heated pad. Rats with an initial baseline mean arterial pressure of less than 55 mmHg or greater than 70 mmHg are excluded. Blood pressure is allowed to stabilize for approximately 10 minutes before a baseline reading is taken. Two initial challenges of proendothelin-1 (0.3 and 1.0 nmol $kg^{-1}$) are administered intravenously in a cumulative fashion and pressor responses recorded. Thereafter, a 55 minute recovery period is allowed and rats in which the blood pressure fails to return to within.20% of the baseline are excluded. Test compound is dosed intravenously at a dose volume of 1.0 ml $kg^{-1}$ body weight and further challenges of proendothelin-1 are administered 5 minutes later. Proendothelin-1 is administered cumulatively in increasing doses (starting at 0.3 nmolkg$^{-1}$) until pressor responses are observed. Endothelin receptor antagonism is quantified by calculating dose ratio shifts at the 30 mmHg change level.

Test D:

This in vivo test involves the measurement of the antagonist effect of the test compound against the pressor response induced by intravenously-administered proendothelin-1 in a conscious rat preparation.

Male rats (260–290 g) are anaesthetised with Saffan administered via the tail vein. The right jugular vein and carotid artery are isolated and catheters filled with heparin implanted. These are exteriorised at the back of the neck using a metal trochar and the neck incision closed with autoclips. Rats are housed individually with free access to food and water during the recovery phase. Later in the day, food is removed and the rats are fasted overnight with free access to water. The following day the rats are placed in perspex restraining tubes and the arterial catheter drained and connected to a pressure transducer for measurement of mean arterial pressure. Following a ten minute stabilization period, proendothelin-1 (usually 0.3–1.0 nmol $kg^{-1}$) is administered cumulatively until a pressor response of 30 mmHg is achieved. The animals are then returned to their cages and allowed to recover for 2 hours. The test compound is administered orally (by gavage) at a known time point during the recovery period. The dose response curve to proendothelin-1 is then repeated at a fixed time after the oral dose (usually 0.5 or 1.0 hours) and again at a further time point (3 or 5 hours). Endothelin receptor antagonism is quantified by calculating dose ratio shifts at the 30 mmHg change level.

By way of illustration of the endothelin receptor antagonist activity of compounds of the formula I, the compound of Example 6 gave the following results in tests A and B described above:

In test A: $pIC_{50}$ 6.5

In test B: $pA_2$ 6.6

The compounds of formula I will generally be administered for therapeutic or prophylactic purposes to warm-blooded animals (including man) requiring such treatment in the form of a pharmaceutical composition, as is well known in the pharmaceutical art. According to a further feature of the invention there is provided a pharmaceutical composition comprising a compound of formula I, or a pharmaceutically acceptable salt thereof as defined above, together with a pharmaceutically acceptable diluent or carrier. The invention also includes pharmaceutical compositions comprising N-(5-chloro-2-pyridyl)-2-naphthalenesulphonamide, N-(5-chloro-2-pyridyl)-1-naphthalenesulphonamide,
N-(5-trifluoromethyl-2-pyridyl)-2-naphthalenesulphonamide or
N-(5-trifluoromethyl-2-pyridyl)-1-naphthalenesulphonamide,
or a pharmaceutically acceptable salt thereof, together with a pharmaceutically acceptable diluent or carrier. Such compositions will conveniently be in a form suitable for oral administration (e.g. as a tablet, capsule, solution, suspension or emulsion) or parenteral administration (e.g. as an injectable aqueous or oily solution, or injectable emulsion).

The compounds of formula I, or a pharmaceutically acceptable salt thereof, may also be advantageously administered for therapeutic or prophylactic purposes together with another pharmacological agent known in the general art to be of value in treating one or more of the diseases or medical conditions referred to hereinabove, such as beta-adrenergic blocker (for example atenolol), a calcium channel blocker (for example nifedipine), an angiotensin converting enzyme (ACE) inhibitor (for example lisinopril), a diuretic (for example furosemide or hydrochlorothiazide), an endothelin converting enzyme (ECE) inhibitor (for example phosphoramidon), a neutral endopeptidase (NEP) inhibitor, an HMGCoA reductase inhibitor, a nitric oxide donor, an anti-oxidant, a vasodilator, a dopamine agonist, a neuroprotective agent, asteroid, a beta-agonist, an anti-coagulant, or a thrombolytic agent. It is to be understood that such combination therapy constitutes a further aspect of the invention.

In general a compound of formula I (or a pharmaceutically acceptable salt thereof as appropriate) will be administered to man so that, for example, a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary, the precise amount of compound (or salt) administered and the route and form of administration depending on size, age and sex of the person being treated and on the particular disease or medical condition being treated according to principles well known in the medical arts.

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will be administered in an analogous amount and manner to those described above for administration to humans. The compounds of formula I are also of value as pharmacological tools in the development and standardisation of test systems for the evaluation of the effects of endothelin in laboratory animals such as cats, dogs, rabbits, monkeys, rats and mice, as part of the continuing search for new and improved therapeutic agents.

The invention will now be illustrated by the following non-limiting Examples in which, unless otherwise stated:
(i) concentrations and evaporations were carried out by rotary evaporation in vacuo;
(ii) operations were carried out at room temperature, that is in the range 18°–26° C.;
(iii) flash column chromatography was performed on Merck Kieselgel 60 (Art. no. 9385) obtained from E Merck, Darmstadt, Germany;
(iv) where a silica gel Mega Bond Elut column is referred to, this means a column containing 10 g of silica of 40 micron particle size, the silica being contained in a 60 ml disposable syringe and supported by a porous disc, obtained from Varian, Harbor City, Calif. U.S.A. under the name "Mega Bond Elut SI"; and
(iv) yields, where given, are intended for the assistance of the reader only and are not necessarily the maximum attainable by diligent process development.

EXAMPLE 1

A solution of 5-dimethylamino-1-naphthalenesulphonyl chloride (1.35 g), 2-amino-5-chloropyridine,(0.64 g), pyridine (0.40 g) and 4-dimethylaminopyridine (20 mg) in dichloromethane (20 ml) was left to stand for 3 days. The solution was divided into two equal portions and each portion was applied to a silica gel Mega Bond Elut column. The columns were eluted with dichloromethane and the appropriate fractions were concentrated by evaporation. The residue was triturated with ether to give 5-(dimethylamino)-N-(5-chloro-2-pyridyl)-1-naphthalenesulphonamide (0.77 g), m.p. 160°–162° C.; mass spectrum [positive fast atom bombardment (+ve FAB), methanol/m-nitrobenzyl alcohol (NBA)]: 362 (M+H)$^+$.

EXAMPLES 2–3

Using an analogous procedure to that described in Example 1, but starting from the appropriate aminopyridine of formula II, the following compounds of formula I were obtained:
(Example 2):
5-(Dimethylamino)-N-(5-methyl-2-pyridyl)-1-naphthalenesulphonamide, m.p. 209°–211° C.; mass spectrum [positive chemical ionisation (+ve CI)]: 342 (M+H)$^+$; starting from 2-amino-5-methylpyridine; and
(Example 3):
5-(Dimethylamino)-N-(5-bromo-2-pyridyl)-1-naphthalenesulphonamide, m.p. 176°–177° C.; mass spectrum (+ve FAB, methanol/NAB): 406 (M+H)$^+$; starting from 2-amino-5-bromopyridine.

EXAMPLE 4

Oil-free sodium hydride (48 mg) was added to a solution of 2-amino-3,5-dichloropyridine (326 mg) in 1,2-dimethoxyethane (20 ml). After evolution of hydrogen ceased, 5-dimethylamino-1-naphthalenesulphonyl chloride (540 mg) was added and the mixture was heated at 75° C. for 3 days. Volatile material was removed by evaporation and the residue was purified by flash chromatography. Elution with dichloromethane/hexane (3:2 v/v) and trituration of the resulting foam with ether/hexane (1:10 v/v) gave 5-(dimethylamino)-N-(3,5-dichloro-2-pyridyl)-1-naphthalenesulphonamide (52 mg), m.p. 161°–163° C.; mass spectrum [+ve FAB, dimethylsulphoxide (DMSO)/glycerol (GLY)]: 396 (M+H)$^+$.

EXAMPLE 5

Sodium hydride (60% dispersion in oil; 160 mg) was added to a solution of 5-dimethylamino-1-naphthalenesulphonamide (500 mg) in N,N-dimethylformamide (30 ml). When evolution of hydrogen ceased, 2-chloro-5-nitropyridine (317 mg) was added and the solution was heated at 95° C. for 18 hours. Volatile material was removed by evaporation and water (50 ml) was added to the residue. The mixture was extracted with ethyl acetate (20 ml), and the aqueous layer was neutralised with 0.05M aqueous acetic acid (40 ml) and extracted with ethyl acetate (3×25 ml). The extracts were washed with water (20 ml) and saturated sodium chloride solution (20 ml) and dried (MgSO$_4$). Volatile material was removed by evaporation and the residue was purified by elution with dichloromethane through a silica gel Mega Bond Elut column. The resulting foam was triturated with ether/hexane (1:1 v/v) to give 5(dimethylamino)-N-(5-nitro-2-Pyridyl)-1-naphthalenesulphonamide (60 mg), m.p. 196° C.; mass spectrum (+ve FAB, methanol/NBA): 373 (M+H)$^+$.

EXAMPLE 6

A solution of 5-dimethylamino-1-naphthalenesulphonyl chloride (269.5 mg), 2-amino-5-bromo-3-methylpyridine (187 mg) and 4-dimethylaminopyridine (100 mg) in pyridine (5 ml) was heated at 85° C. for 18 hours. Volatile material was removed by evaporation and dichloromethane (50 ml) was added. Insoluble material was removed by filtration and the filtrate was concentrated by evaporation. The residue was purified by flash chromatography, eluting with ethyl acetate/hexane (1:1 v/v), to give 5-(dimethylamino)-N-(5-bromo-3-methyl-2-pyridyl)-1-naphthalenesulphonamide as a foam (135 mg); NMR (CDCl$_3$): 2.2(s, 3H), 2.9(s, 6H), 7.15 (d, 1H), (7.4–7.8(m, 4H), 8.4(d, 1H), 8.5(d, 2H); mass spectrum (+ve CI): 420 (M+H)$^+$.

EXAMPLE 7

Using an analogous procedure to that described in Example 6, but using a proportionate amount of 2-amino-5-trifluoromethylpyridine in place of 2-amino-5-bromo-3-methylpyridine, there was thus obtained 5-(dimethylamino)-N-(5-trifluoromethyl-2-pyridyl)-1-naphthalenesulphonamide, m.p. 185°–186° C.; mass spectrum (+ve FAB, DMSO/methanol/NBA): 396 (M+H)$^+$.

EXAMPLE 8

Using an analogous procedure to that described in Example 6, but using a proportionate amount of 2-amino-5-iodopyridine in place of 2-amino-5-bromo-3-methylpyridine and carrying out the reaction at ambient temperature, there was thus obtained 5-(dimethylamino)-N-(5-iodo-2-pyridyl)-1-naphthalenesulphonamide, m.p. 211°–212° C.; mass spectrum (+ve FAB, DHSO/GLY): 454(M+H)$^+$.

EXAMPLE 9

Using an analogous procedure to that described in Example 1, but using a proportionate amount of 6-amino-3-bromo-2-methylpyridine in place of 2-amino-5-chloropyridine, there was thus obtained 5-(dimethylamino)-N-(5-bromo-6-methyl-2-pyridyl)-1-naphthalenesulphonamide, m.p. 155°–156° C. mass spectrum (+ve CI): 420 (M+H)$^+$.

EXAMPLE 10 (Note: all parts by weight)

The compounds of the invention may be administered for therapeutic or prophylactic use to warm-blooded animals such as man in the form of conventional pharmaceutical compositions, typical examples of which include the following:

| a) Capsule (for oral administration) | |
|---|---|
| Active ingredient* | 20 |
| Lactose powder | 578.5 |
| Magnesium stearate | 1.5 |
| b) Tablet (for oral administration) | |
| Active ingredient* | 50 |
| Microcrystalline cellulose | 400 |
| Starch (pregelatinised) | 47.5 |
| Magnesium stearate | 2.5 |
| c) Injectable Solution (for intravenous administration) | |
| Active ingredient* | 0.05–1.0 |
| Propylene glycol | 5.0 |
| Polyethylene glycol (300) | 3.0–5.0 |
| Purified water | to 100% |
| d) Injectable Suspension (for intramuscular administration) | |
| Active ingredient* | 0.05–1.0 |
| Methylcellulose | 0.5 |
| Tween 80 | 0.05 |
| Benzyl alcohol | 0.9 |
| Benzalkonium chloride | 0.1 |
| Purified water | to 100% |

Note: the active ingredient * may typically be an Example described hereinbefore or as a pharmaceutically acceptable salt. Tablets and capsules formulations may be coated in conventional manner in order to modify or sustain dissolution of the active ingredient. Thus, for example, they may be coated with a conventional enterically digestible coating.

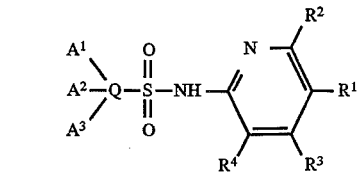

I

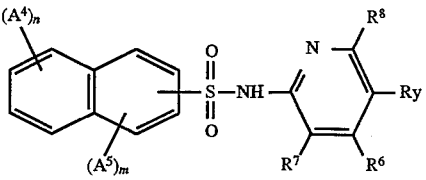

Ia

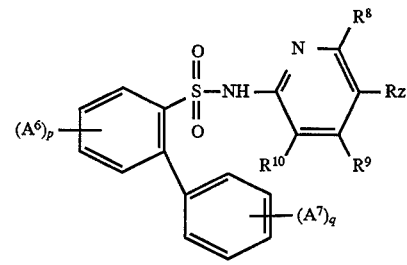

Ib

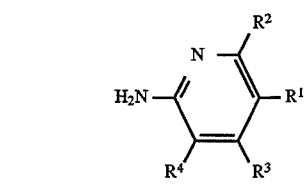

II

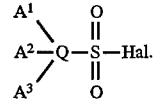

III $$\begin{array}{c} A^1 \\ A^2-Q-S-ORe \\ A^3 \quad O \end{array} \quad \text{IIIa}$$

$$\text{IV}$$ (structure with L, N, R¹, R³, R⁴)

$$\begin{array}{c} A^1 \\ A^2-Q-S-NH_2 \\ A^3 \quad O \end{array} \quad \text{V}$$

$$\text{VI}$$ (structure with T, sulfonamide, pyridyl R¹, R², R³, R⁴)

What I claim is:

1. A compound of the formula I $$\begin{array}{c} A^1 \\ A^2-Q-S-NH- \\ A^3 \quad O \end{array} \quad \text{I}$$ (with pyridyl bearing R¹, R², R³, R⁴)

wherein Q is a naphthyl or biphenyl group;

A¹, A² and A³ are attached to a phenyl or benzene ring of Q and are independently selected from hydrogen, (1–6C)alkyl, amino(1–6C)alkyl, hydroxy(1–6C)alkyl, N-[(1–4C)alkyl]amino(1–6C)alkyl, N,N-[di(1–4C)alkyl]amino(1–6C)alkyl, (2–6C)alkenyl, (2–6C)alkynyl, halogeno(1–6C)alkyl, (1–6C)alkoxy, dihalogeno(1–6C)alkoxy, trihalogeno(1–6C)alkoxy, (2–6C)alkenyloxy, (1–4C)alkoxy(1–6C)alkyl, (1–4C) alkylthio(1–6C)alkyl, (1–4C)alkylsulphinyl(1–6C) alkyl, (1–4C)alkylsulphonyl(1–6C)alkyl, (1–4C) alkylenedioxy, (3–6C)cycloalkyl, (3–8C)cycloalkyl (1–6C)alkyl, phenyl, phenyl(1–6C)alkyl, phenoxy, phenyl(1–6C)alkoxy, halogeno, hydroxy, mercapto, cyano, nitro, carboxy, (1–6C)alkoxycarbonyl, (2–6C) alkenyloxycarbonyl, phenyloxycarbonyl, phenyl (1–6C)alkoxycarbonyl, (1–6C)alkanoyl, benzoyl, (1–6C)alkylthio, (1–6C)alkylsulphinyl, (1–6C) alkylsulphonyl, phenylthio, phenylsulphinyl, phenylsulphonyl, (1–6C)alkanoylamino, trifluoroacetyl, trifluoroacetamido, N-[(1–4C)alkyl]trifluoroacetamido, benzamido, N-[(1–4C)alkyl]benzamido, carbamoyl, (1–4C) alkylcarbamoyl, di-(1–4C)alkylcarbamoyl, phenylcarbamoyl, sulphamoyl, N-(1–4C)alkylsulphamoyl, N, N-di(1–4C)alkylsulphamoyl, N-phenylsulphamoyl, (1–6C)alkanesulphonamido, benezenesulphonamido, ureido, 3-(1–6C)alkylureido, 3-phenylureido, thioureido, 3-(1–6C)alkylthioureido, 3-phenylthioureido and a group —NRaRb in which Ra and Rb are independently selected from hydrogen, (1–6C)alkyl, phenyl(1–4C)alkyl and (1–6C)alkyl bearing a carboxy or (1–4C)alkoxycarbonyl group, or the group —NRaRb taken together complete a 1-pyrrolidinyl, 2oxo-1-pyrrolidinyl, 1-piperidinyl or 2oxo-1-piperidinyl ring;

R², R³ and R⁴ have any of the values defined above for A¹, A² or A³;

R¹ is selected from (1–6C)alkyl, amino(1–6C)alkyl, hydroxy(1–6C)alkyl, N-[(1–4C)alkyl]amino(1–6C)alkyl, N, N-[di(1–4C)alkyl]amino(1–6C)alkyl, (2–6C)alkenyl, 2-[(1–6C)alkoxycarbonyl]ethenyl, 2-phenylethenyl, (2–6C)alkynyl, (1–6C)alkoxycarbonylethynyl, phenylethynyl, halogeno(1–6C)alkyl, (1–3C)alkoxy, dihalogeno(1–3C)alkoxy, trihalogeno(1–3C)alkoxy, (2–6C)alkenyloxy, (1–4C)alkoxy(1–6C)alkyl, (1–4C) alkylthio(1–6C)alkyl, (1–4C)alkylsulphinyl(1–6C) alkyl, (1–4C)alkylsulphonyl(1–6C)alkyl, (3–6C) cycloalkyl, (3–8C)cycloalkyl(1–6C)alkyl, phenyl (1–6C)alkyl, phenyl(1–3C)alkoxy, halogeno, hydroxy, mercapto, nitro, (1–6C)alkanoyl, benzoyl, (1–6C) alkylthio, (1–6C)alkylsulphinyl, (1–6C) alkylsulphonyl, phenylthio, phenylsulphinyl, phenylsulphonyl, (1–6C)alkanoylamino, trifluoroacetyl, trifluoroacetamido, N-[(1–4C)alkyl]trifluoroacetamido, benzamido, N-[(1–4C)alkyl]benzamido, carbamoyl, (1–4C) alkylcarbamoyl, di-(1–4C)alkylcarbamoyl, phenylcarbamoyl, sulphamoyl, N-(1–4C)alkylsulphamoyl, N, N-di(1–4C)alkylsulphamoyl, N-phenylsulphamoyl, (1–6C)alkanesulphonamido, benezenesulphonamido, ureido, 3-(1–6C)alkylureido, 3-phenylureido, thioureido, 3-(1–6C)alkylthioureido, 3-phenylthioureido and a group —NRaRb in which Ra and Rb are independently selected from hydrogen, (1–6C)alkyl, phenyl(1–4C)alkyl and (1–6C)alkyl bearing a carboxy or (1–4C)alkoxycarbonyl group, or the group —NRaRb taken together complete a 1-pyrrolidinyl, 2oxo-1-pyrrolidinyl, 1-piperidinyl or 2oxo-1-piperidinyl ring; or R¹ together with the adjacent R² or R³ is (3–5C)alkylene or (3–5C)alkenylene which together with the carbon atoms to which R¹ and R² or R³ are attached complete a 5–7 membered ring;

and wherein any of said phenyl, naphthyl or benzene moieties of A¹, A², A³, R¹, R², R³ or R⁴ may be unsubstituted or bear one or two substituents independently selected from (1–4C)alkyl, (1–4C)alkoxy, halogeno, cyano and trifluoromethyl; or a pharmaceutically-acceptable salt thereof; but excluding N-(5-chloro-2-pyridyl)-2-naphthalenesulphonamide, N-(5-chloro-2-pyridyl)-1-naphtalensulphonamide, N-(5-trifluoromethyl-2-pyridyl)-2-naphthalenesulphonamide, N-(5-iodo-2-pyridyl)-4-acetamido-1-naphthalenesulphonamide, N-(5-iodo-2-pyridyl)-4amino-1-naphthalenesulphonamide, N-[4,5-bis(trifluoromethyl)-2pyridyl]-2-naphthalenesulphonamide, N-(5-iodo-2-pyridyl)-6-acetamido-2-naphthalenesulphonamide, N-(5-iodo-2-pyridyl)-6-amino-2-naphthalenesulphonamide, and N-(5-trifluoromethyl)-2-pyridyl-1-naphthalenesulphonamide.

2. A compound as claimed in claim 1 wherein A¹, A², A³, R², R³ and R⁴ are independently selected from hydrogen, methyl, ethyl, propyl, isopropyl, sec-butyl, aminomethyl, 2-aminoethyl, hydroxymethyl, 1-hydroxyethyl, 2-hydroxyethyl, methylaminomethyl, methylaminoethyl, dimethylaminomethyl, 2-(dimethylamino)ethyl, vinyl, allyl, 1-propenyl, 2-butenyl, ethynyl, 1-propynyl, 2-propynyl, 1-butynyl, chloromethyl, bromomethyl, fluoromethyl, dichloromethyl, difluoromethyl, trifluoromethyl, 2,2,2-trifluoroethyl, pentafluoroethyl, methoxy, ethoxy, propoxy, isopropoxy, butoxy, difluoromethoxy, trifluoroethoxy, 2,2,2-trifluoroethoxy, 3,3,3-trifluoropropoxy, vinyloxy, allyloxy, 1-propenyloxy, 2-butenyloxy, methoxymethyl, ethoxymethyl, 1-methoxyethyl, 2-methoxyethyl, 2-ethoxyethyl, 3-methoxypropyl, methylthiomethyl, 1-methylthioethyl, 2-methylthioethyl, 2-methylthioprop-2-yl, ethylthiomethyl, 1-ethylthioethyl, 2-ethylthioethyl, 2-ethylthioprop-2-yl, methylsulphinylmethyl, 1-methylsulphinylethyl, 2-methylsulphinylethyl, 2-methylsulphinylprop-2-yl, ethylsulphinylmethyl, 1-ethylsulphinylethyl, 2-ethylsulphinylethyl, 2-ethylsulphinylprop-2-yl, methylsulphonylmethyl, 1-methylsulphonylethyl, 2-methylsulphonylethyl, 2-methylsulphonylprop-2-yl, ethylsulphonylmethyl, 1-ethylsulphonylethyl, 2-ethylsulphonylethyl, 2-ethylsulphonylprop-2-yl, methylenedioxy, ethylenedioxy, isopropylidenedioxy, cyclopropyl, cyclobutyl, cyclopentyl, cyclopropylmethyl, cyclopropylethyl, cyclobutylmethyl, cyclopentylmethyl, phenyl, benzyl, 1-phenylethyl, 2-phenylethyl, phenoxy, benzyloxy, 1-phenylethoxy, 2-phenylethoxy, 2-phenylpropoxy, 3-phenylpropoxy, fluoro, chloro, bromo, iodo, hydroxy, mercapto, cyano, nitro, carboxy, methoxycarbonyl, ethoxycarbonyl, propoxycarbonyl, allyloxycarbonyl, 2-methyl-2-propenyloxycarbonyl, 3-methyl-3-butenyloxycarbonyl, phenyloxycarbonyl, benzyloxycarbonyl, 1-phenylethoxycarbonyl, 2-phenylethoxycarbonyl, formyl, acetyl, propionyl, benzoyl, methylthio, ethylthio, methylsulphinyl, ethylsulphinyl, methylsulphonyl, ethylsulphonyl, phenylthio, phenylsulphinyl, phenylsulphonyl, formamido, acetamido, propionamido, trifluoroacetyl, trifluoroacetamido, N-methyltrifluoroacetamide, N-ethyltrifluoroacetamide, benzamido, N-methylbenzamido, N-ethylbenzamido, carbamoyl, N-methylcarbamoyl, N-ethylcarbamoyl, N,N-dimethylcarbamoyl, N,N-diethylcarbamoyl, phenylcarbamoyl, sulphamoyl, N-methylsulphamoyl, N-ethylsulphamoyl, N,N-dimethylsulphamoyl, N,N-diethylsulphamoyl, N-phenylsulphamoyl, methanesulphonamido, ethanesulphonamido, benzenesulphonamido, ureido, 3-methylureido, 3-ethylureido, 3-propylureido, 3-phenylureido, thioureido, 3-methylthioureido, 3-ethylthioureido, 3-propylthioureido, and a group —NRaRb in which Ra and Rb are independently selected from hydrogen, methyl, ethyl, propyl, benzyl, 1-phenylethyl, 2-phenylethyl, carboxymethyl, carboxyethyl, methoxycarbonylmethyl, methoxycarbonylethyl, ethoxycarbonylethyl, methoxycarbonylpropyl and ethoxycarbonylpropyl, or the group —NRaRb taken together complete a 1-pyrrolidinyl, 2-oxo-1-pyrrolidinyl, 1-piperidinyl or 2oxo-1-piperidinyl ring; $R^1$ is selected from methyl, ethyl, propyl, isopropyl, sec-butyl, aminomethyl, 2-aminoethyl, hydroxymethyl, 1-hydroxyethyl, 2-hydroxyethyl, methylaminomethyl, methylaminoethyl, dimethylaminomethyl, 2-(dimethylamino)ethyl, vinyl, allyl, 1-propenyl, 2-butenyl, 2-methoxycarbonylethenyl, 2-ethoxycarbonylethenyl, 2-phenylethenyl, ethynyl, 1-propynyl, 2-propynyl, 1-butynyl, methoxycarbonylethynyl, ethoxycarbonylethynyl, phenylethynyl, chloromethyl, bromomethyl, fluoromethyl, dichloromethyl, difluoromethyl, trifluoromethyl, 2,2,2-trifluoroethyl, pentafluoroethyl, methoxy, ethoxy, difluoromethoxy, trifluoroethoxy, 2,2,2-trifluoroethoxy, 3,3,3-trifluoropropoxy, vinyloxy, allyloxy, 1-propenyloxy, 2-butenyloxy, methoxymethyl, ethoxymethyl, 1-methoxyethyl, 2-methoxyethyl, 2-ethoxyethyl, 3-methoxypropyl, methylthiomethyl, 1-methylthioethyl, 2-methylthioethyl, 2-methylthioprop-2-yl, ethylthiomethyl,y 1-ethylthioethyl, 2-ethylthioethyl, 2-ethylthioprop-2-yl, methylsulphinylmethyl, 1-methylsulphinylethyl, 2-methylsulphinylethyl, 2-methylsulphinylprop-2-yl, ethylsulphinylmethyl, 1-ethylsulphinylethyl, 2-ethyl-sulphinylethyl, 2-ethylsulphinylprop-2-yl, methylsulphonylmethyl, 1-methylsulphonylethyl, 2-methylsulphonylethyl, 2-methylsulphonylprop-2-yl, ethylsulphonylmethyl, 1-ethylsulphonylethyl, 2-ethyl-sulphonylethyl, 2-ethylsulphonylprop-2-yl, cyclopropyl, cyclobutyl, cyclopentyl, cyclopropylmethyl, cyclopropylethyl, cyclobutylmethyl, cyclopentylmethyl, benzyl, 1-phenylethyl, 2-phenylethyl, phenoxy, benzyloxy, 1-phenylethoxy, 2-phenylethoxy, fluoro, chloro, bromo, iodo, hydroxy, mercapto, nitro, formyl, acetyl, propionyl, benzoyl, methylthio, ethylthio, methylsulphinyl, ethylsulphinyl, methylsulphonyl, ethylsulphonyl, phenylthio, phenylsulphinyl, phenylsulphonyl, formamido, acetamido, propionamido, trifluoroacetyl, trifluoroacetamido, N-methyltrifluoroacetamide, N-ethyltrifluoroacetamide, benzamido, N-methylbenzamido, N-ethylbenzamido, carbamoyl, N-methylcarbamoyl, N-ethylcarbamoyl, N,N-dimethylcarbamoyl, N,N-diethylcarbamoyl, phenylcarbamoyl, sulphamoyl, N-methylsulphamoyl, N-ethylsulphamoyl, N,N-dimethylsulphamoyl, N,N-diethylsulphamoyl, N-phenylsulphamoyl, methanesulphonamido, ethanesulphonamido, benzenesulphonamido, ureido, 3-methylureido, 3-ethylureido, 3-propylureido, 3-phenylureido, thioureido, 3-methylthioureido, 3-ethylthioureido, 3-propylthioureido, 3-phenylthioureido and a group —NRaRb in which Ra and Rb are independently selected from hydrogen, methyl, ethyl, propyl, benzyl, 1-phenylethyl, 2-phenylethyl, carboxymethyl, carboxyethyl, methoxycarbonylmethyl, methoxycarbonylethyl, ethoxycarbonylethyl, methoxycarbonylpropyl and ethoxycarbonylpropyl or the group —NRaRb taken together complete a 1-pyrrolidinyl, 2-oxo-1-pyrrolidinyl, 1-piperidinyl or 2oxo-1-piperidinyl ring; or $R^1$ together with the adjacent $R^2$ or $R^3$ is trimethylene, tetramethylene, 1-propenylene or 2-propenylene;

and wherein any of said phenyl, naphthyl or benzene moieties of $A^1$, $A^2$, $A^3$, $R^1$, $R^2$, $R^3$ or $R^4$ may be unsubstituted or bear one or two substituents independently selected from methyl, ethyl, methoxy, ethoxy, fluoro, chloro, bromo, iodo, cyano and trifluoromethyl; or a pharmaceutically-acceptable salt thereof.

3. A compound as claimed in claim 1 in which $R^1$ is selected from halogeno, (1–4C)alkyl, trifluoromethyl and nitro.

4. A compound as claimed in claim 1 or 3 in which $R^2$, $R^3$ and $R^4$ are independently selected from hydrogen, halogeno, (1–4C)alkoxy and (1–4C)alkyl.

5. A compound of the formula Ia

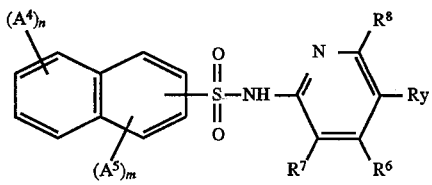

wherein Ry is selected from halogeno, (1–4C)alkyl, trifluoromethyl and nitro; m is zero; n is 1; $A^4$ is selected from (i) (1–4C)alkanoylamino; (ii) the group —NRaRb in which Ra and Rb are the same and are selected from methyl, ethyl, and propyl; (iii) the group —NRaRb in which one of Ra and Rb is methyl and the other is ethyl or propyl; and (iv) the group —NRaRb in which one of Ra and Rb is hydrogen and the other is methyl, ethyl, propyl, isopropyl, isobutyl or sec-butyl; which group $A^4$ is attached at the 5-position of the naphthyl ring, which ring is attached to the sulphonamido moiety at the 1-position of the naphthyl ring; and $R^5$, $R^6$ and $R^7$ are independently selected from hydrogen, halogeno, (1–4C)alkyl; or a pharmaceutically-acceptable salt thereof.

6. A compound of formula Ib

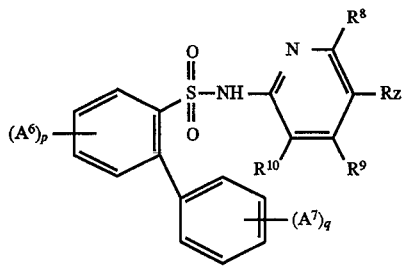

wherein Rz is selected from halogeno, (1–4C)alkyl, trifluoromethyl and nitro; p=zero; q=1 or 2; $R^8$, $R^9$ and $R^{10}$ are independently selected from hydrogen, halogeno, (1–4C)alkyl; and $A^7$ is selected from hydrogen, methyl, ethyl, propyl, isopropyl, sec-butyl, aminomethyl, 2-aminoethyl, hydroxymethyl, 1-hydroxyethyl, 2-hydroxyethyl, methylaminomethyl, methylaminoethyl, dimethylaminomethyl, 2-(dimethylamino)ethyl, vinyl, allyl, 1-propenyl, 2-butenyl, ethynyl, 1-propynyl, 2-propynyl, 1-butynyl, chloromethyl, bromomethyl, fluoromethyl, dichloromethyl, difluoromethyl, trifluoromethyl, 2,2,2-trifluoroethyl, pentafluorethyl, methoxy, ethoxy, propoxy, isopropoxy, butoxy, difluormethoxy, trifluoroethoxy, 2,2,2-trifluoroethoxy, 3,3,3-trifluoropropoxy, vinyloxy, allyloxy, 1-propenyloxy, 2butenyloxy, methoxymethyl, ethoxymethyl, 1-methoxyethyl, 2-methoxyethyl, 2-ethoxyethyl, 3-methoxypropyl, methylthiomethyl, 1-methylthioethyl, 2-methylthioethyl, 2-methylthioprop-2-yl, ethylthiomethyl, 1-ethylthioethyl, 2-ethylthioethyl, 2-ethylthioprop-2-yl, methylsulphinylmethyl, 1-methylsulphinylethyl, 2-methylsulphinylethyl, 2-methylsulphinylprop-2-yl, ethylsulphinylmethyl, 1-ethylsulphinylethyl, 2-ethylsulphinylethyl, 2-ethylsulphinylprop-2-yl, methylsulphonylmethyl, 1-methylsulphonylethyl, 2-methylsulphonylethyl, 2-methylsulphonylprop-2-yl, ethylsulphonylmethyl, 1-ethylsulphonylethyl, 2-ethylsulphonylethyl, 2-ethylsulphonylprop-2-yl, methylenedioxy, ethylenedioxy, isopropylidenedioxy, cyclopropyl, cyclobutyl, cyclopentyl, cyclopropylmenthyl, cyclopropylethyl, cyclobutylmethyl, cyclopentylmethyl, phenyl, benzyl, 1-phenylethyl, 2-phenylethyl, phenoxy, benzyloxy, 1-phenylethoxy, 2-phenylethoxy, 2-phenylpropoxy, 3-phenylpropoxy, fluoro, chloro, bromo, iodo, hydroxy, mercapto, cyano, nitro, carboxy, methoxycarbonyl, ethoxycarbonyl, propoxycarbonyl, allyloxycarbonyl, 2-methyl-2-propenyloxycarbonyl, 3-methyl-3-butenyloxycarbonyl, phenyloxycarbonyl, benzyloxycarbonyl, 1-phenylethoxycarbonyl, 2-phenylethoxycarbonyl, formyl, acetyl, propionyl, benzoyl, methylthio, ethylthio, methylsulphinyl, ethylsulphinyl, methylsulphonyl, ethylsulphonyl, phenylthio, phenylsulphinyl, phenylsulphonyl, formamido, acetamido, propionamido, trifluoroacetyl, trifluoroacetamido, N-methyltrifluoroacetamide, N-ethyltrifluoroacetamide, benzamido, N-methylbenzamido, N-ethylbenzamido, carbamoyl, N-methylcarbamoyl, N-ethylcarbamoyl, N,N-dimethylcarbamoyl, N,N-diethylcarbamoyl, phenylcarbamoyl, sulphamoyl, N-methylsulphamoyl, N-ethylsulphamoyl, N,N-dimethylsulphamoyl, N,N-diethylsulphamyl, N-phenylsulphamoyl, methanesuphonamido, ethnesulphonamido, benzenesulphonamido, ureido, 3-methylureido, 3-ethylureido, 3-phenylureido, thioureido, 3-methylthioureido, 3-ethylthioureido, 3-propylthioureido, and a group —NRaRb in which Ra and Rb are independently selected from hydrogen, methyl, ethyl, propyl, 1-phenylethyl, 2-phenylethyl, carboxymethyl, carboxyethyl, methoxycarbonylmethyl, methoxycarbonylethyl, ethoxycarbonylethyl, methoxycarbonylpropyl and ethoxycarbonylpropyl, or the group —NRaRb taken together complete a 1-pyrrolidinyl, 2-oxo-1-piperidinyl or 2-oxo-1-piperidinyl ring;

wherein any of said phenyl, naphthyl or benzene moieties of $A^7$ may be unsubstituted or bear one or two substituents independently selected from methyl, ethyl, methoxy, ethoxy, fluoro, chloro, bromo, iodo, cyano and trifluoromethyl;

or a pharmaceutically acceptable salt thereof.

7. A compound of the formula I selected from:

5-(dimethylamino)-N-(5-chloro-2-pyridyl)-1-naphthalenesulphonamide;

5-(dimethylamino)-N-(5-bromo-2-pyridyl)-1-naphthalenesulphonamide;

5-(dimethylamino)-N-(5-bromo-3-methyl-2-pyridyl)-1-naphthalenesulphonamide; and 5-(dimethylamino)-N-(5-trifluoromethyl-2-pyridyl)-1-naphthalenesulphonamide;

or a pharmaceutically acceptable salt thereof.

8. A salt as claimed in claim 1 which is selected from salts with bases forming physiologically acceptable cations and, for those compounds which are sufficiently basic, salts with acids forming physiologically acceptable anions.

9. A pharmaceutical composition which comprises a compound of the formula I, or a pharmaceutically acceptable salt thereof, as claimed in claim 1, or the compound N-(5-chloro-2-pyridyl)-2-naphthalenesulphonamide, N-(5-chloro-2-pyridyl)-1-naphthalenesulphonamide, N-(5-trifluoromethyl-2pyridyl)-2-naphthalenesulphonamide, N-(5-iodo-2-pyridyl)-4-acetamido-1- naphtylenesulphonamide, N-(5-iodo-2-pyridyl)-4amino-1-naphthalenesulphonamide, N-(5-iodo-2-pyridyl)-6-acetamido-2-naphthalenesulphonamide, N-(5-iodo-2-pyridyl)-6-amino-2-naphthalenesulphonamide or N-(5-trifluoromethyl)-1-naphthalenesulphonamide or a pharmaceutically acceptable salt thereof, together with a pharmaceutically acceptable diluent or carrier.

10. A method of antagonising one or more of the actions of endothelin in a human or other warm-blooded animal requiring such treatment which comprises administering to said human or other warm-blooded animal an antagonistically effective amount of a compound of formula I, or a pharmaceutically-acceptable salt thereof, as claimed in claim 1.

* * * * *